(12) United States Patent
Dominelli et al.

(10) Patent No.: US 6,777,948 B2
(45) Date of Patent: Aug. 17, 2004

(54) METHOD AND APPARATUS FOR DETECTING WEAR IN COMPONENTS OF HIGH VOLTAGE ELECTRICAL EQUIPMENT

(75) Inventors: Nicola Dominelli, Coquitlam (CA); Hans Schellhase, Delta (CA); David W. Casson, Langley (CA); Edward A. Hall, Delta (CA)

(73) Assignee: Electric Power Research Institute, Inc., Palo Alto, CA (US)

( * ) Notice: Subject to any disclaimer, the term of this patent is extended or adjusted under 35 U.S.C. 154(b) by 0 days.

(21) Appl. No.: 10/241,108

(22) Filed: Sep. 11, 2002

(65) Prior Publication Data

US 2004/0046563 A1 Mar. 11, 2004

(51) Int. Cl.⁷ .............................................. G01N 27/60
(52) U.S. Cl. ...................................... 324/455; 324/456
(58) Field of Search ................................. 324/455, 456, 324/557, 600, 536, 420

(56) References Cited

U.S. PATENT DOCUMENTS

| | | | | |
|---|---|---|---|---|
| 3,715,598 A | * | 2/1973 | Tomlin, Jr. | 250/395 |
| 5,389,792 A | * | 2/1995 | DiMarzio et al. | 250/370.06 |
| 5,453,591 A | | 9/1995 | Stroud | 218/43 |
| 5,844,331 A | | 12/1998 | Kieser et al. | 307/137 |
| 6,023,036 A | | 2/2000 | Nichols | 218/91 |

* cited by examiner

*Primary Examiner*—Jay Patidar
*Assistant Examiner*—Vincent Q. Nguyen
(74) *Attorney, Agent, or Firm*—Morgan, Lewis & Bockius LLP (57) ABSTRACT

A tracer material is embedded in a component of electrical equipment to detect excessive wear of the component when it is exposed to an electrical arc. As the component wears, the tracer material becomes exposed to the electrical arc and emits electromagnetic radiation, which is monitored continuously. The tracer material is selected so that it emits electromagnetic radiation when it is exposed to an electrical arc that is distinct from electromagnetic radiation emitted by any other parts of the component.

18 Claims, 9 Drawing Sheets

METHOD AND APPARATUS FOR DETECTING WEAR IN COMPONENTS OF HIGH VOLTAGE ELECTRICAL EQUIPMENT

BACKGROUND OF THE INVENTION

1. Field of the Invention

The invention relates generally to high voltage electrical equipment. More specifically, the invention is directed to detecting wear in components of high voltage electrical equipment that are regularly exposed to electrical arcing.

2. Description of Related Art

Load tap changers, voltage regulators, circuit breakers and switches are used to interrupt power. The surfaces of some of their components are eroded by being regularly exposed to electrical arcing and mechanical friction during the course of their normal operation. Equipment failure results if these components are allowed to wear out to the extent that their electrical and mechanical integrity is compromised. Components most susceptible to erosion are the arcing metal contacts and TEFLON nozzles in sulfur hexafluoride ($SF_6$) gas circuit breakers.

It is desirable to know when components of electrical equipment have become dangerously worn out without taking the equipment out of service to perform an internal inspection. Several approaches have been used to accomplish this. One approach is installing fiber optic strands into the electrical contacts of the electrical equipment. As the contacts wear, the fiber optic strands become exposed to light emitted from electrical arcing, which may be detected by a photodiode or other sensor placed at the opposite ends of the fiber optic strands. Installing fiber optic strands in electrical contacts is expensive, however, and the fiber optic strands are subject to breakage as a result of mechanical stress. Another approach embeds tracer materials at predetermined depths in the electrical contacts or below the surface of a TEFLON nozzle of a $SF_6$ circuit breaker. When the electrical contacts wear to the point that the tracer materials are exposed, the tracer materials are released into the insulating medium or else are decomposed by the electrical arc. In order to determine whether wear has proceeded beyond a safe level, the insulating medium must be withdrawn and analyzed periodically for the presence of the tracer elements or the products from their decomposition. This approach is not suitable for continuous monitoring of the electrical equipment.

Based on the foregoing, there is a need for a way to continuously monitor for excessive wear of the components of electrical equipment that are susceptible to erosion by being exposed to electrical arcing and mechanical friction.

SUMMARY OF THE INVENTION

Accordingly, it is an object of the present invention to detect excessive wear in components of electrical equipment by monitoring them continuously.

This object and other objects are provided by the present invention, one embodiment of which comprises a method of monitoring a component of an electrical device for wear by exposing a component having a tracer material embedded in it at a predetermined depth to an electrical arc, wearing the component until the tracer material is exposed to the electrical arc, and detecting electromagnetic radiation emitted by the tracer material when the tracer material is exposed to the electrical arc. The electromagnetic radiation emitted by the tracer material is distinct from electromagnetic radiation emitted by any other parts of the component; for example, it may have a different wavelength. The component is preferably monitored continuously to detect electromagnetic radiation emitted by the tracer material. Another embodiment of the present invention comprises a method of manufacturing a component of a device in which an electrical arc may be generated wherein the method involves embedding a tracer material within the component at a predetermined depth.

Yet another embodiment of the present invention comprises an apparatus for detecting wear in an electrical device in which a tracer material is embedded at a predetermined depth within a component of the electrical device. As in the other embodiments, the tracer material emits electromagnetic radiation when the tracer material is exposed to an electrical arc that is distinct from electromagnetic radiation emitted by any other parts of the component; for example, it may have a different wavelength. The apparatus preferably includes an electromagnetic detector, such as a photodiode having a narrow bandwidth filter or spectrophotometer, to continuously monitor the component for electromagnetic radiation emitted by the tracer material. A fiber optic cable may be used to transmit the electromagnetic radiation to the electromagnetic detector. Suitable tracer materials include lithium, cobalt, niobium and rare earth metals, such as yttrium. In addition, multiple tracer materials may be embedded at multiple pre-determined depths and/or at pre-selected locations within the component in order to detect the extent and/or location of wearing in the component.

These and other objects and features of the invention will appear from the following description from which the preferred embodiments are set forth in detail in conjunction with the accompanying drawings.

DETAILED DESCRIPTION OF THE PREFERRED EMBODIMENTS

The structure and function of the preferred embodiments can best be understood by reference to the drawings. The reader will note that the same reference designations appear in multiple locations. Where this is the case, the numerals refer to the same or corresponding structure in those locations.

Figure 1:
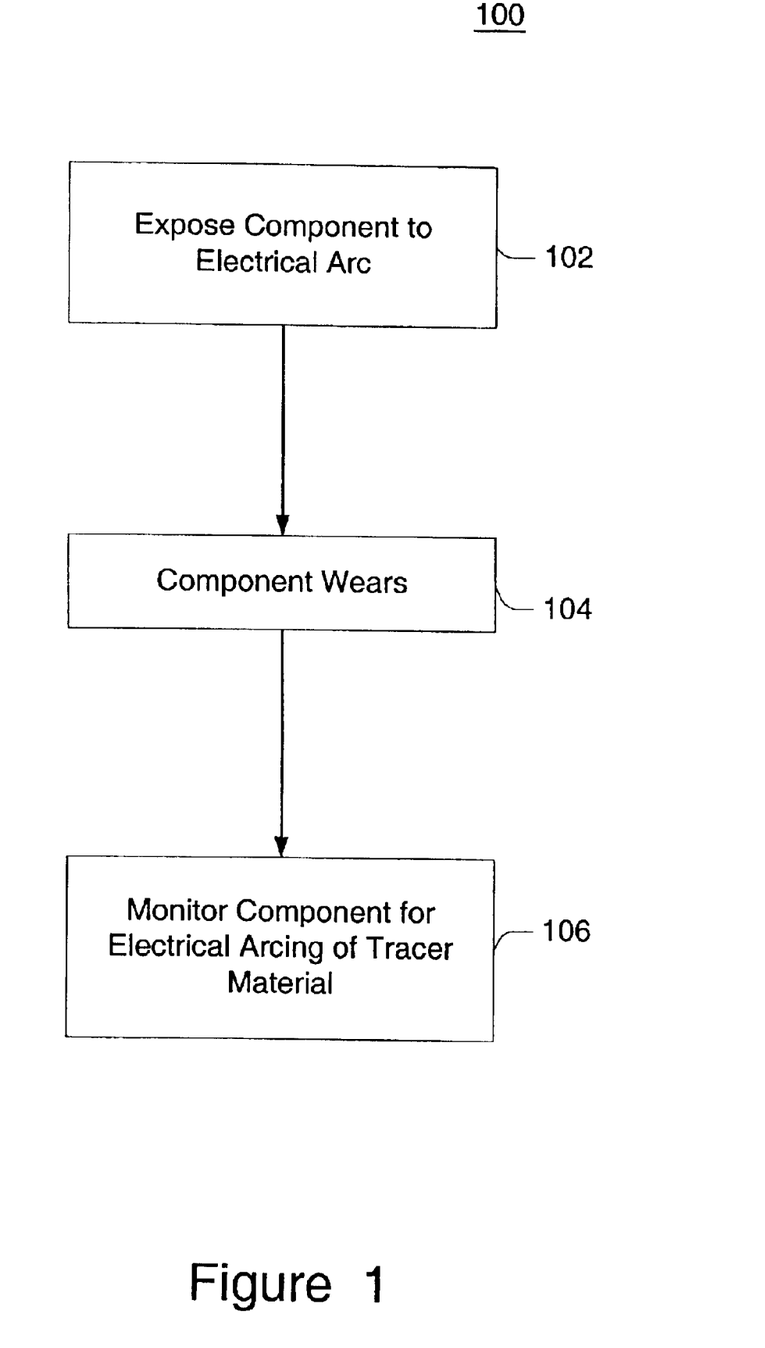
FIG. 1 is a flowchart of a method for detecting wear in a component of an electrical device in accordance with an embodiment of the invention.

FIG. 1 shows a flowchart 100 for detecting wear in a component of an electrical device in accordance with an embodiment of the present invention. In step 102 the component, which contains a tracer material embedded in it at a predetermined depth, is exposed to an electrical arc. In step 104 the component wears as a result of the exposure to the electrical arc or other causes, such as mechanical friction. Lastly, the component is continuously monitored for electromagnetic radiation from the tracer material in step 106; the tracer material emits electromagnetic radiation when the component is sufficiently worn so that the embedded tracer material itself is exposed to the electric arc. The tracer material is embedded in the component preferably during the manufacturing of the component, but the tracer material may also be embedded in existing components after they have been manufactured.

Figure 2:
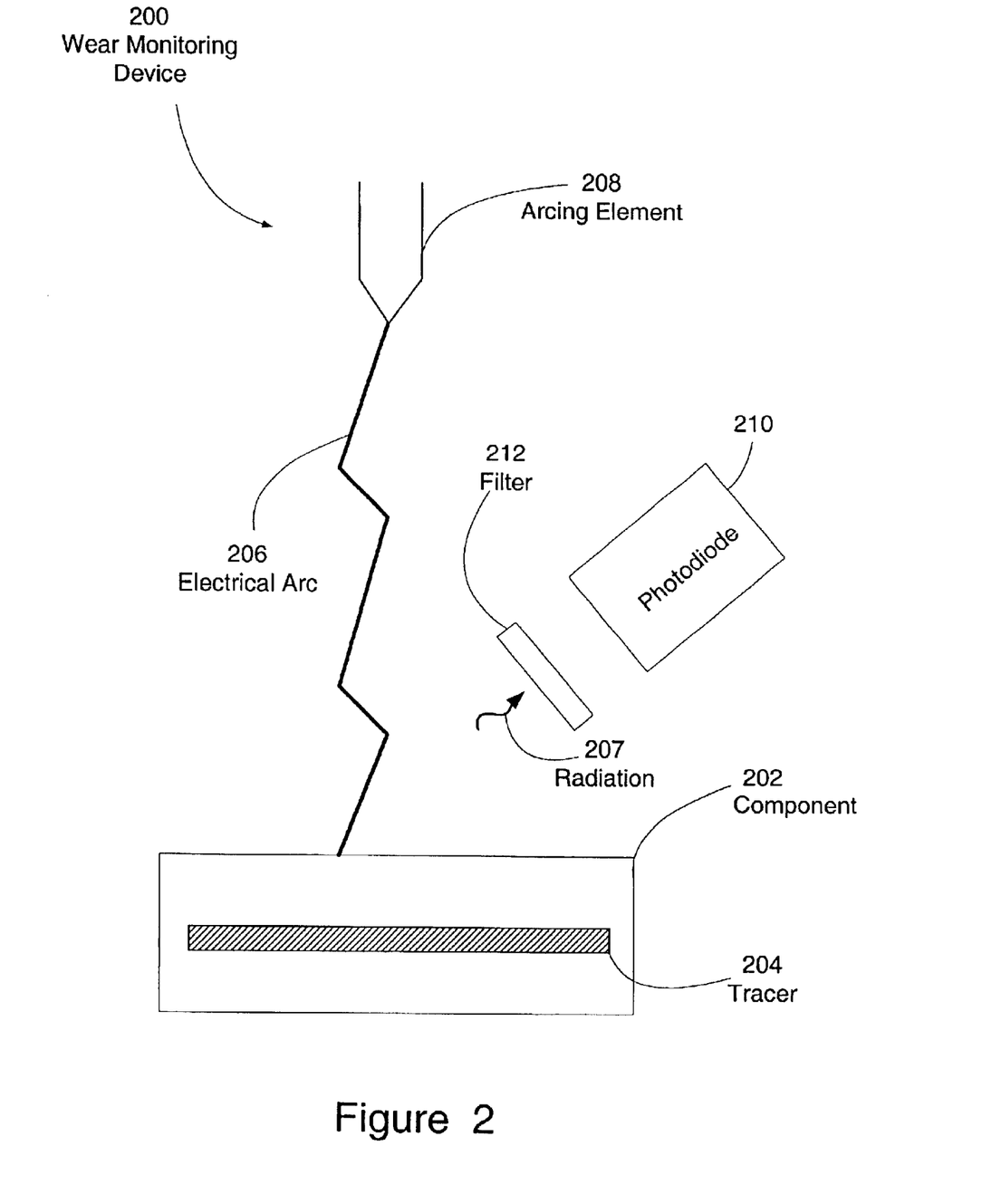
FIG. 2 is a schematic of an apparatus for detecting wear in a component of an electrical device in accordance with an embodiment of the invention.
Figure 3:
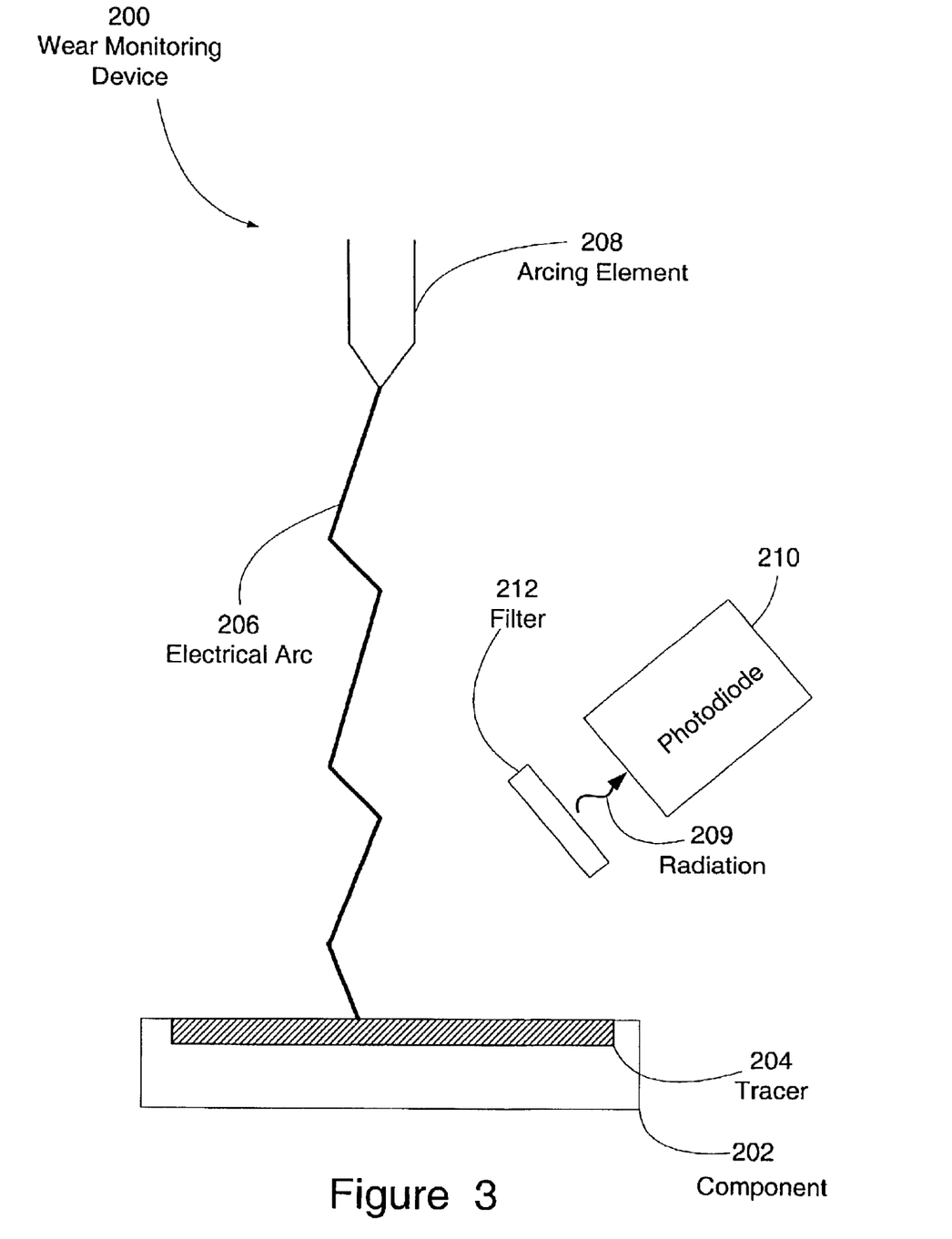
FIG. 3 is a schematic of the apparatus in FIG. 2 at a later time after the component has been worn to expose a tracer material.

FIGS. 2 and 3 are schematics of an apparatus 200 for detecting wear in a component 202 of an electrical device in accordance with an embodiment of the present invention. FIG. 2 illustrates the apparatus 200 at an initial time, and FIG. 3 illustrates the apparatus at a later time. As shown in FIG. 2, a component 202 of an electrical device (not shown) has a tracer material 204 embedded in it at a predetermined depth. The component 202 is exposed to an electrical arc 206 that is generated by an electrical arcing element 208. The high temperature of the electrical arc 206 causes the portion of the component 202 that is exposed to the electrical arc 206 to emit electromagnetic radiation 207 that is continuously monitored by an electromagnetic detector, which may be a photodiode 210 or any other suitable detector for electromagnetic radiation (such as a spectrophotometer). In the embodiment shown in FIG. 2, a narrow band filter 212 is placed between the photodiode 210 and the component 202 of the electrical device so that the photodiode 210 is allowed to detect electromagnetic radiation having a wavelength in the narrow band that can pass through the narrow band filter 212. As shown in FIG. 2, the electromagnetic radiation 207 has not been transmitted through the narrow band filter 212 because the electromagnetic radiation 207 was not emitted by the tracer material 204. The electromagnetic detector is capable of monitoring the component 202 of the electrical device continuously during the operation of the electrical device.

FIG. 3 is a schematic of the apparatus 200 in FIG. 2, but at a later time after the component 202 has been worn. In contrast to FIG. 2, FIG. 3 shows the tracer material 204 on a surface of the component 202, instead of embedded in the component at a predetermined depth. At the later time illustrated in FIG. 3, the surface of the component 202 has been worn away as a result of exposure to the electrical arc 206 or other causes, such as mechanical friction, so that the tracer material 204 is exposed to the electrical arc 206. The high temperature of the electrical arc 206 causes the tracer material 204 to emit electromagnetic radiation 209. The tracer material 204 is selected so that when it is exposed to the electrical arc 206, it emits electromagnetic radiation 209 that is distinct from the electromagnetic radiation 207 (FIG. 2) emitted by any other parts of the component that are exposed to the electrical arc. For example, lithium, which emits red light corresponding to a wavelength of approximately 670.7 nm, may be a suitable tracer material in some applications. It is desirable for the tracer material 204 to be chemically and thermally stable under the operating conditions for the component. It may also be desirable for the tracer material 204 not to affect the dielectric properties of any fluid medium in the electrical device in which it is to be used. Among the materials that may be suitable for use as a tracer material in accordance with this invention are lithium, cobalt, niobium and rare earth metals such as yttrium. As shown in FIG. 3, the electromagnetic radiation 209 has been transmitted through the narrow band filter 212 because the electromagnetic radiation 209 was emitted by the tracer material 204.

In the embodiment shown in FIGS. 2 and 3, the electromagnetic radiation emitted by the tracer material 204 when it is exposed to the electrical arc 206 is detected by a photodiode 210 after the electromagnetic radiation has passed through a narrow band filter 212. The narrow band filter removes electromagnetic radiation with a wavelength outside the narrow band that is transmitted by the narrow band filter 212. The narrow band filter 212 is selected so that it transmits electromagnetic radiation that is emitted by the tracer material when it is exposed to the electrical arc, but not electromagnetic radiation emitted by other parts of the component 202.

Figure 4:
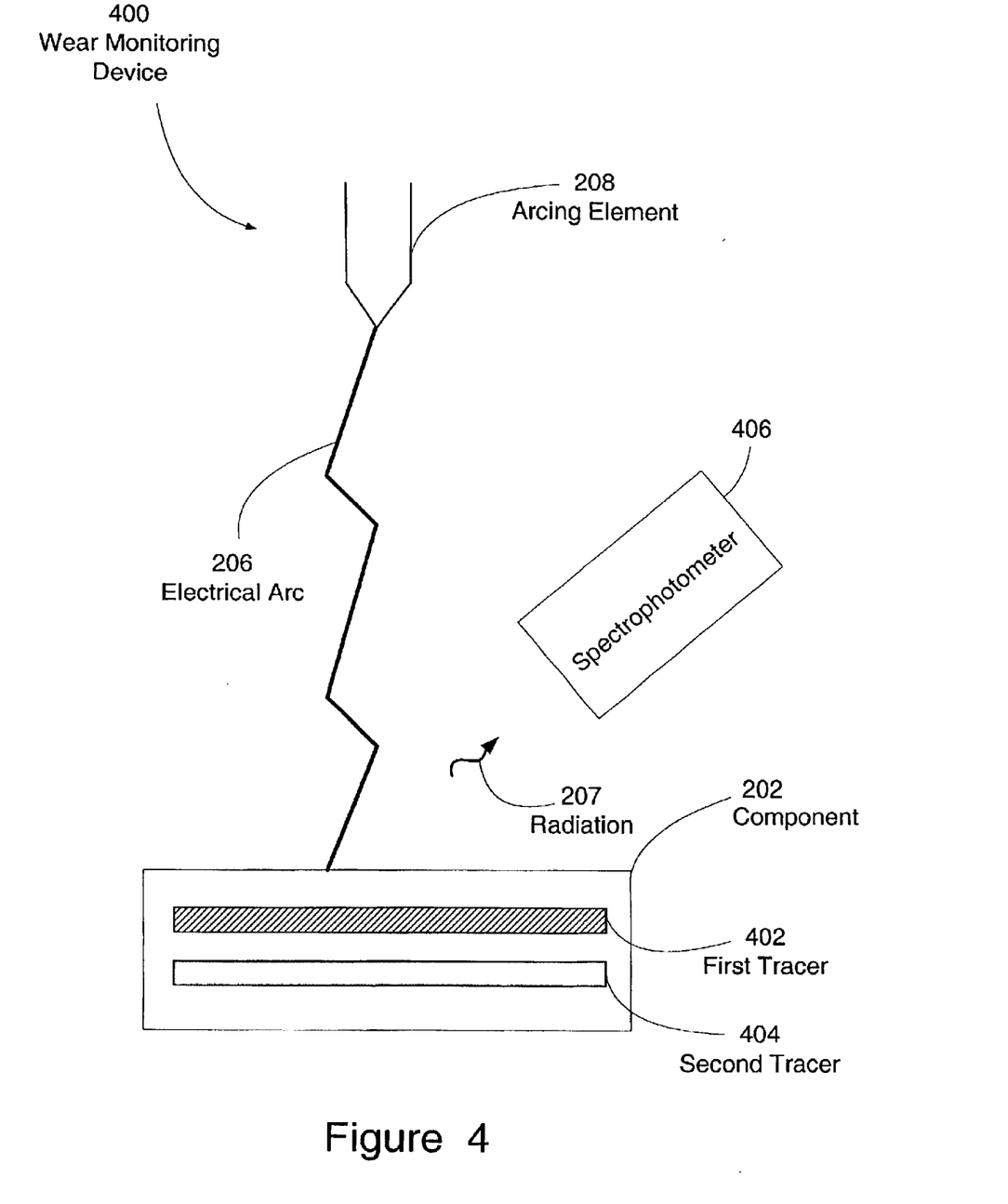
FIG. 4 is a schematic of an apparatus for detecting two amounts of wear in a component of an electrical device in accordance with an alternate embodiment of the invention.

FIG. 4 is a schematic of an apparatus 400 for detecting two amounts of wear in a component 202 of an electrical device in accordance with an alternate embodiment of the present invention. As shown in FIG. 4, a first tracer material 402 is embedded at one depth within the component 202 and a second tracer material 404 is embedded at another depth within the component 202. The first tracer material 402 and the second tracer material 404 are selected so that when they are exposed to the electrical arc 206, they emit electromagnetic radiation that is distinct from each other as well as from the radiation emitted by any other parts of the component that are exposed to the electrical arc. A spectrophotometer 406 analyzes electromagnetic radiation from the component 202 to determine whether the surface of the component 202 has worn to expose either the first tracer material 402 or the second tracer material 404. Alternatively, two photodiodes with differing narrow band filters may be used to monitor electromagnetic radiation from the first tracer material 402 and the second tracer material 404. Additional tracer materials (not shown) may be imbedded in the component 202 at various depths and/or at different locations in order to estimate the extent and/or location of wear of the component 202 according to which of the tracer materials is exposed to the electrical arc 206.

Figure 5:
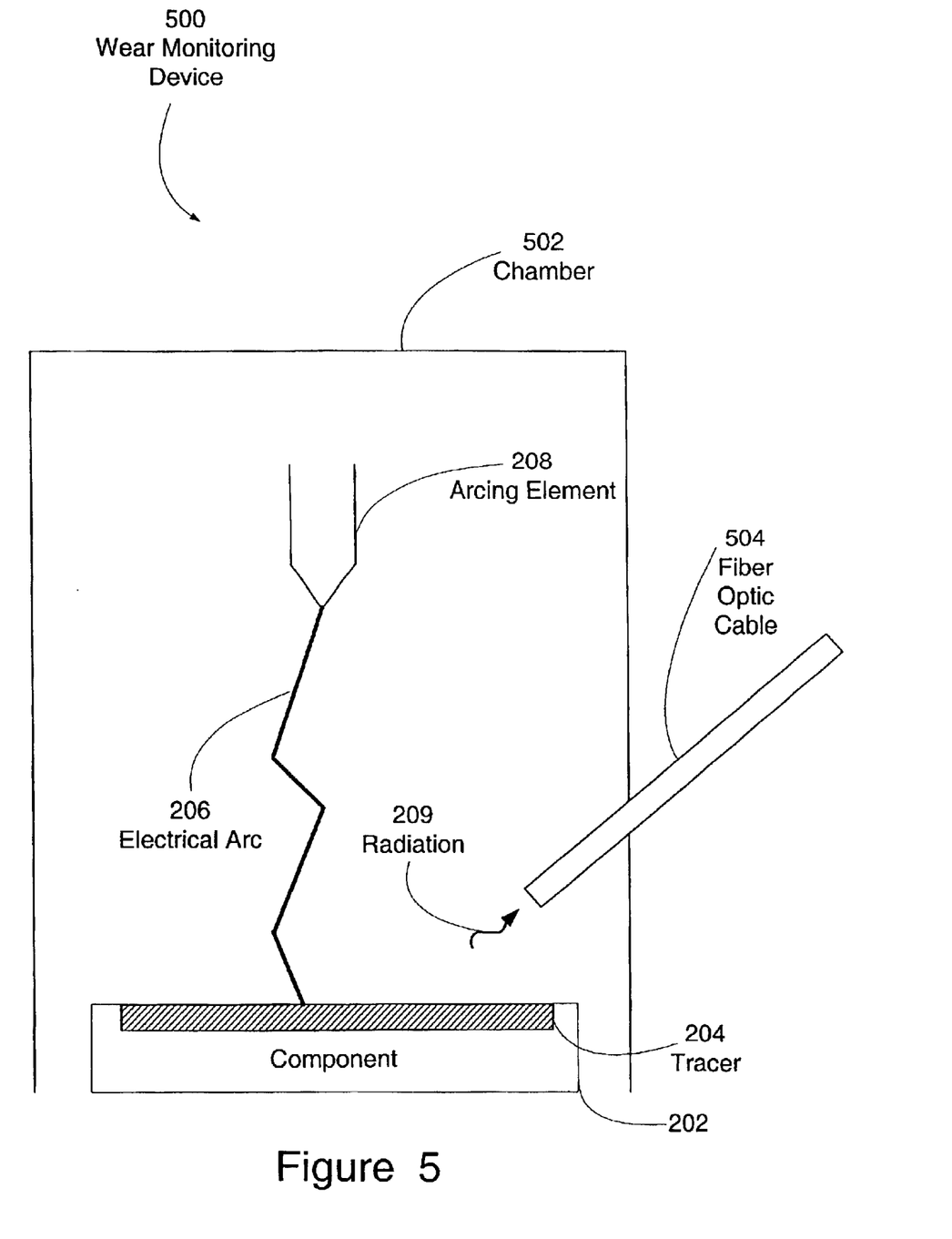
FIG. 5 is a schematic of an apparatus for detecting wear in a component of an electrical device in accordance with an alternate embodiment of the invention.

FIG. 5 is a schematic of an apparatus 500 for detecting wear in a component 202 of an electrical device in accordance with an alternate embodiment of the present invention. In the embodiment shown in FIG. 5, an arcing element 208 and a component 202 having an embedded tracer material 204 are placed in an equipment chamber 502 and a fiber optic cable 504 is used to transmit electromagnetic radiation emitted by the component to an electromagnetic detector (not shown) outside the equipment chamber 502.

The invention having been described, the following are examples of use of the present invention and are presented to illustrate, rather than to limit the scope of the invention. The following examples illustrate a apparatus for detecting wear in a load tap changer and a circuit breaker according to the present invention. Other equipment in which this invention could be used include voltage regulators and $SF_6$ gas circuit breakers.

Figure 6:
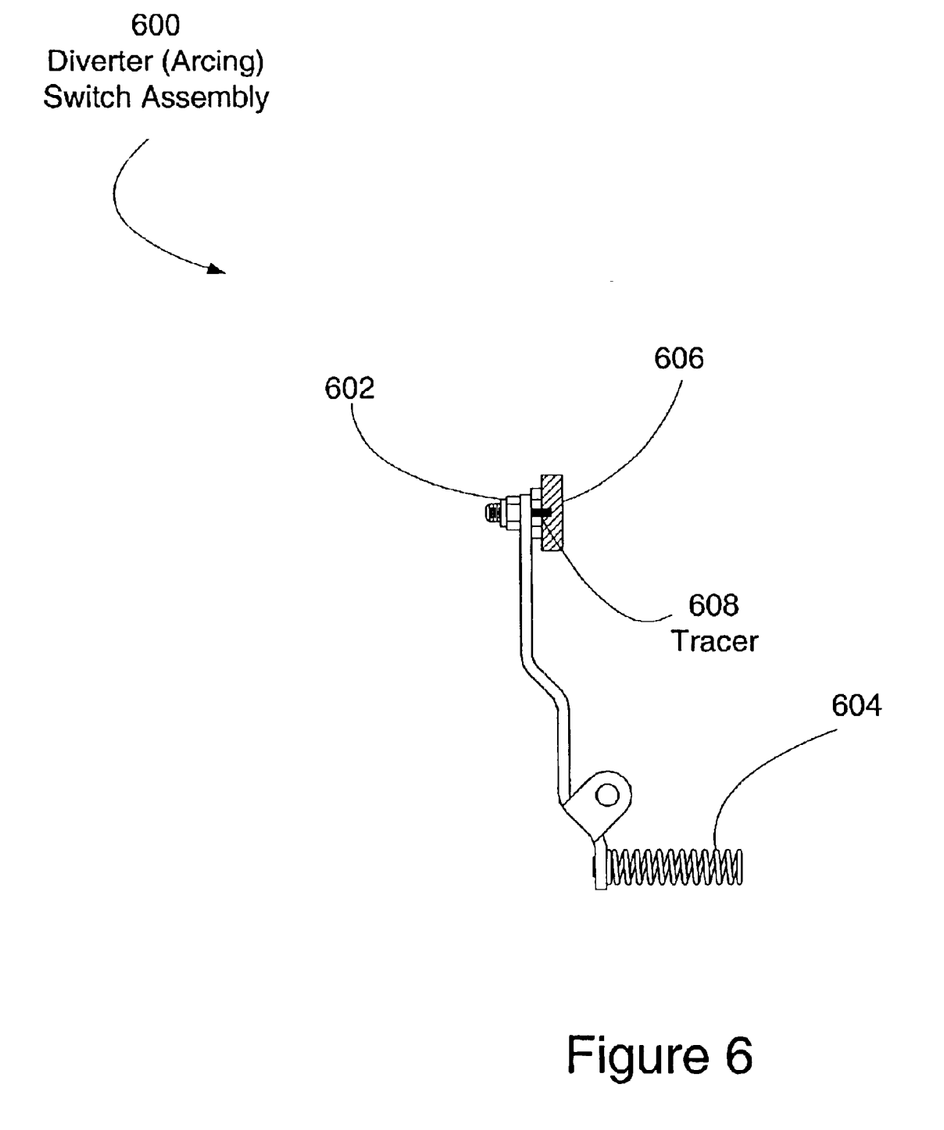
FIG. 6 is a diagram showing a cross-sectional view of components of a load tap changer in accordance with an embodiment of the invention.

FIG. 6 is a cross-sectional view of a diverter switch assembly 600 of a load tap changer in accordance with an embodiment of the invention. The diverter switch assembly 600 includes an arcing contact tip assembly 602 at one end of the diverter switch assembly and a compression spring 604 at its opposite end. The arcing contact tip assembly 602 may include an elkonite contact 606. As shown in FIG. 6, tracer material 608 is embedded within the elkonite contact 606. In accordance with the present invention, the tracer material 608 will become exposed to an electrical arc (not shown) after the surface of the elkonite contact 606 is worn away, and an electromagnetic detector (not shown) will detect the distinctive electromagnetic radiation emitted by the tracer material 608.

Figure 7:
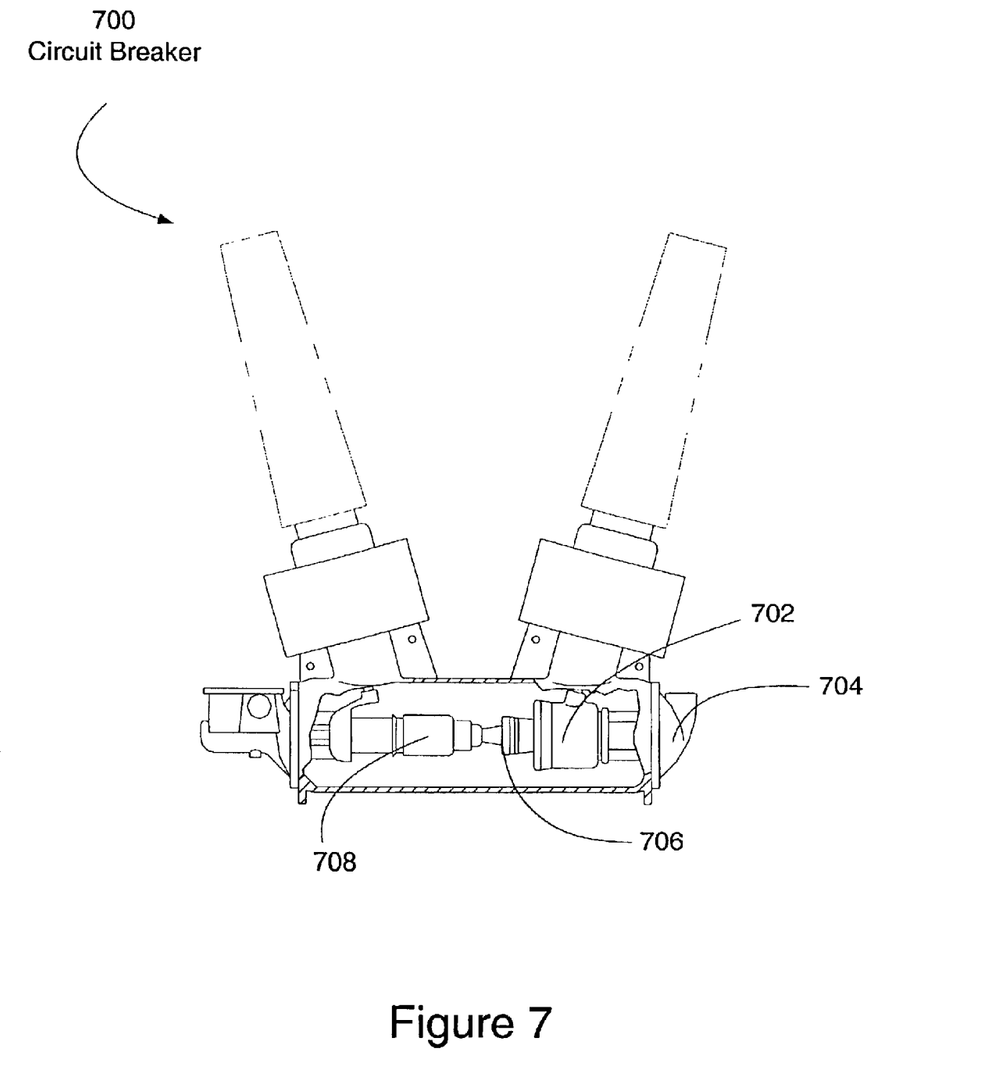
FIG. 7 is a diagram showing a partially cut away cross-sectional view of components of a circuit breaker in accordance with an embodiment of the invention.
Figure 8:
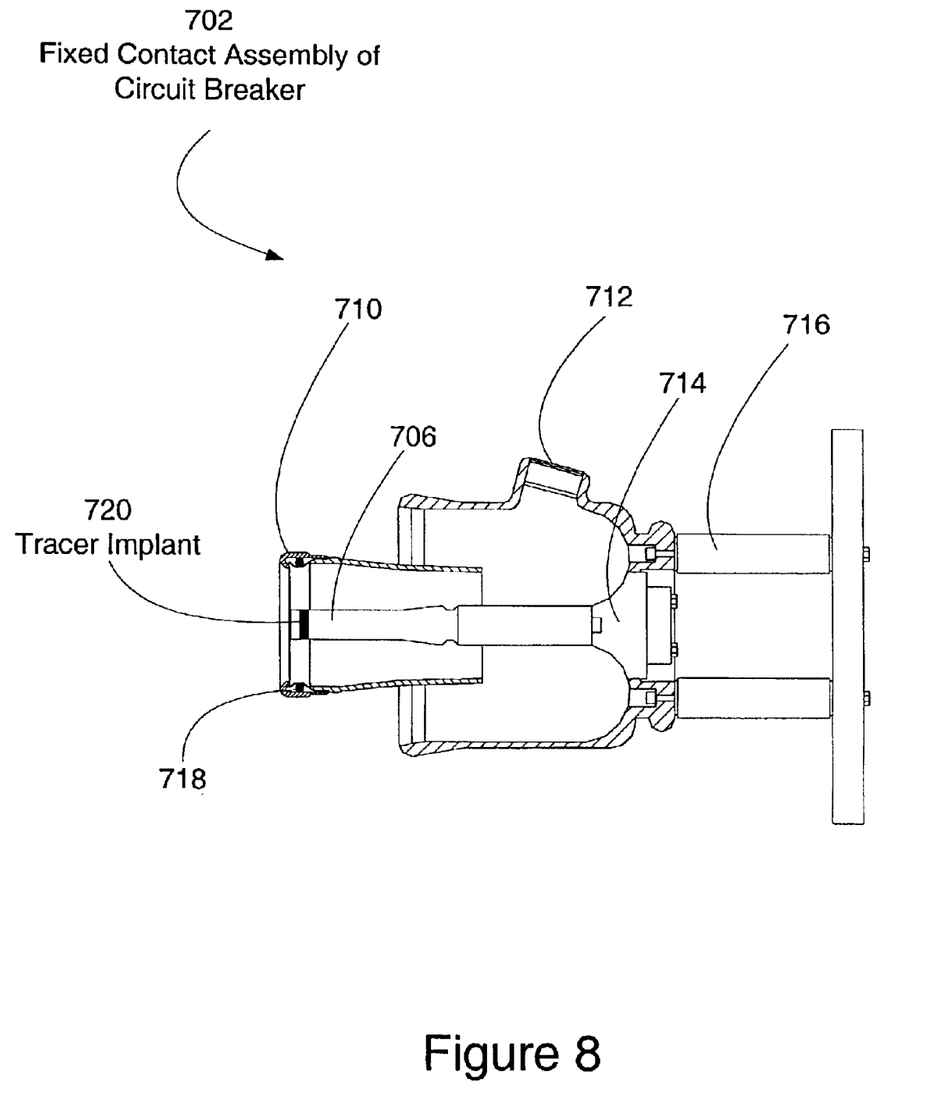
FIG. 8 is a diagram showing a partially cut away cross-sectional view of the fixed contact assembly of a circuit breaker in accordance with an embodiment of the invention.
Figure 9:
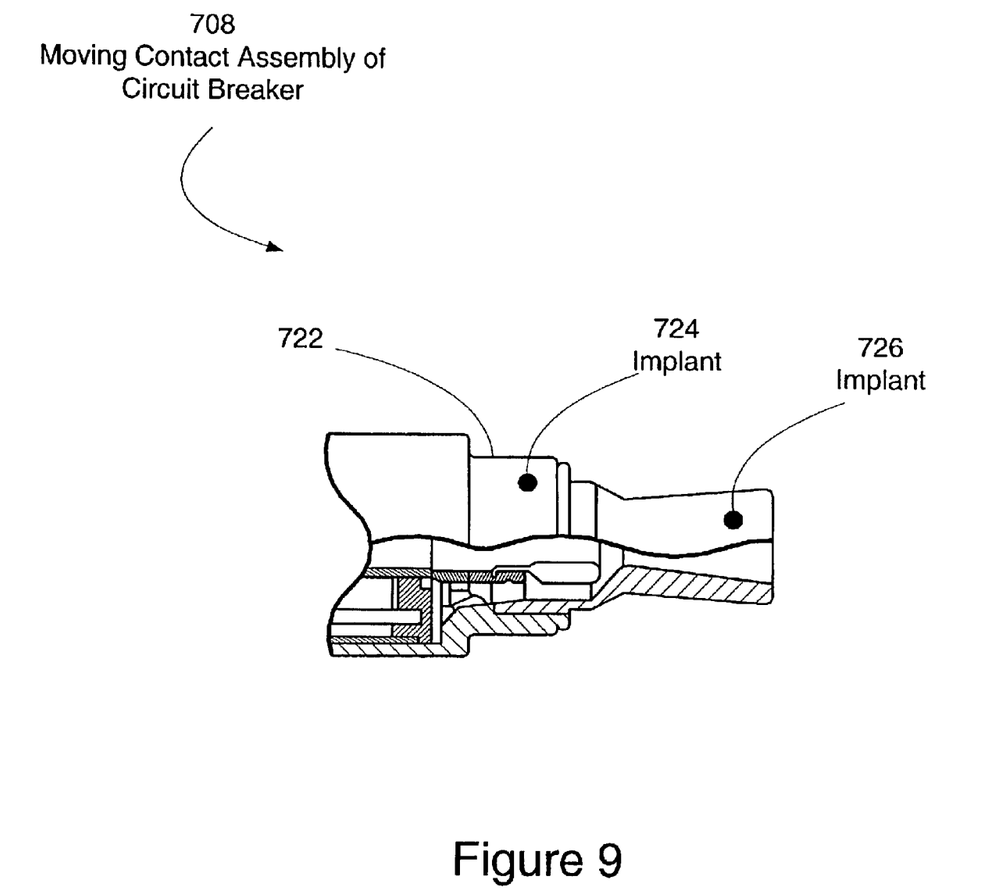
FIG. 9 is a diagram showing a partially cut away cross-sectional view of the moving contact assembly of a circuit breaker in accordance with an embodiment of the invention.

FIGS. 7, 8 and 9 are, respectively, partially cut away cross-sectional views of a circuit breaker 700, the fixed contact assembly 702 of the circuit breaker 700, and the moving contact assembly 708 of the circuit breaker 700 in accordance with an embodiment of the invention. FIG. 7 shows a circuit breaker 700, comprised of a fixed contact assembly 702 with a fixed contact pin 706, a tank 704, and a moving contact assembly 708.

FIG. 8 shows a fixed contact assembly 702 of a circuit breaker 700, comprised of shielding 710, a multicontact liner and a clamping ring 712, a contact pin holder 714, insulating support 716, a contact crown 718, and a fixed contact pin 706. As shown in FIG. 8, tracer material 720 is embedded within the fixed contact pin 706. In accordance with the present invention, the tracer material 720 will become exposed to an electrical arc (not shown) after the surface of the fixed contact pin 706 is worn away, and an electromagnetic detector (not shown) will detect the distinctive electromagnetic radiation emitted by the tracer material 720.

FIG. 9 shows a moving contact assembly 708 of a circuit breaker 700, comprised of a main contact 722. As shown in FIG. 8, tracer materials 724 and 726 are embedded within the main contact 722. In accordance with the present invention, the tracer materials 724 and 726 will become exposed to an electrical arc (not shown) after the surface of the main contact 722 is worn away, and an electromagnetic detector (not shown) will detect the distinctive electromagnetic radiation emitted by the tracer materials 724 and 726.

Various embodiments of the invention have been described. The descriptions are intended to be illustrative of the present invention. It will be apparent to one of skill in the art that modifications may be made to the invention as described without departing from the scope of the claims set out below. For example, it is to be understood that although the invention has been described using a photodiode with a narrow band filter as an example of an electromagnetic radiation detector, any suitable electromagnetic radiation detector may be used by the present invention. Furthermore, it is to be understood that although the invention has been illustrated with particular examples of a load tap changer and a circuit breaker, any component of electrical equipment that is exposed to an electrical arc is contemplated to fall within the scope of the invention.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. The presently disclosed embodiments are therefore to be considered in all respects as illustrative and not restrictive, the scope of the invention being indicated by the appended claims, and not limited to the foregoing description.

What is claimed is:

1. A method for detecting wear in a component of an electrical device, comprising:
   exposing a component of an electrical arc to an electrical arc, wherein the component has a tracer material embedded at a predetermined depth;
   wearing the component such that the tracer material is exposed to the electric arc;
   emitting electromagnetic radiation from the tracer material upon exposure to the electrical arc; and
   detecting electromagnetic radiation emitted by the tracer material.

2. The method of claim 1, wherein emitting electromagnetic radiation comprises emitting electromagnetic radiation that is distinct from electromagnetic radiation emitted by any other parts of the component when the component is exposed to the electrical arc.

3. The method of claim 1, further comprising monitoring the component continuously to detect the electromagnetic radiation emitted by the tracer material.

4. The method of claim 1, further comprising embedding a tracer material in the component at a predetermined depth.

5. A method for manufacturing a component of a device in which an electrical arc may be generated, comprising:
   embedding a tracer material in a component of a device at a predetermined depth;
   wherein the tracer material emits electromagnetic radiation distinct from electromagnetic radiation emitted by any other parts of the component when the tracer material is exposed to an electrical arc.

6. The method of claim 5, wherein the tracer material is selected from the group consisting of lithium, cobalt, niobium, and a rare earth metal.

7. An apparatus for detecting wear in an electrical device, comprising:
   a component of a device that is exposed to an electrical arc;
   a tracer material embedded at a predetermined depth in the component, wherein the tracer material is capable of emitting electromagnetic radiation when exposed to the electrical arc and the electromagnetic radiation emitted by the tracer material is distinct from electromagnetic radiation emitted by any other parts of the component when the component is exposed to the electrical arc; and
   an electromagnetic detector configured to monitor the component for the electromagnetic radiation emitted by the tracer material.

8. The apparatus of claim 7, wherein the electromagnetic detector is configured to monitor continuously.

9. The apparatus of claim 8, wherein the electromagnetic detector is a photodiode having a narrow band electromagnetic radiation filter.

10. The apparatus of claim 8, wherein the electromagnetic detector is a spectrophotometer.

11. The apparatus of claim 7, further comprising a fiber optic cable configured to transmit the electromagnetic radiation to the electromagnetic detector.

12. The apparatus of claim 7, wherein the tracer material is selected from the group consisting of lithium, cobalt, niobium, and a rare earth metal.

13. An apparatus for detecting wear in an electrical device, comprising:

a component of a device that is exposed to an electrical arc;

a first tracer material embedded at a first predetermined depth within the component, wherein the first tracer material emits a first electromagnetic radiation when exposed to the electrical arc that is distinct from electromagnetic radiation emitted by any other parts of the component when the component is exposed to the electrical arc; and a second tracer material embedded at a second predetermined depth within the component, wherein the second tracer material emits a second electromagnetic radiation when exposed to the electrical arc that is distinct from the first electromagnetic radiation and any other parts of the component when the component is exposed to the electrical arc.

14. The apparatus of claim 13, further comprising an electromagnetic detector configured to monitor the component continuously for the first electromagnetic radiation emitted by the first tracer material and for the second electromagnetic radiation emitted by the second tracer material.

15. The apparatus of claim 13, further comprising:

a first electromagnetic detector configured to monitor the component for the first electromagnetic radiation emitted by the first tracer material; and a second electromagnetic detector configured to monitor the component for the second electromagnetic radiation emitted by the second tracer material.

16. The apparatus of claim 15, wherein the first electromagnetic detector and the second electromagnetic detector are configured to monitor the component continuously.

17. An apparatus for detecting wear in an electrical device, comprising:

a component of a device that is exposed to an electrical arc;

a tracer material embedded at a predetermined depth in the component, wherein the tracer material emits electromagnetic radiation having a predetermined wavelength when the tracer material is exposed to the electrical arc that is different from any wavelength of electromagnetic radiation emitted by any other parts of the component when the component is exposed to the electrical arc; and a photodiode having a narrow band electromagnetic radiation filter to detect the electromagnetic radiation having the predetermined wavelength, wherein the photodiode is configured to monitor the component continuously.

18. A system for detecting wear in an electrical device, comprising:

a component of a device that is exposed to an electrical arc;

a tracer material embedded at a predetermined depth in the component, wherein the tracer material is capable of emitting electromagnetic radiation when exposed to the electrical arc and the electromagnetic radiation emitted by the tracer material is distinct from electromagnetic radiation emitted by any other parts of the component when the component is exposed to the electrical arc; and an electromagnetic detector configured to monitor the component for the electromagnetic radiation emitted by the tracer material.

* * * * *